United States Patent

Teissier et al.

[11] Patent Number: 5,849,957
[45] Date of Patent: Dec. 15, 1998

[54] PROCESS FOR OBTAINING ISOPHORONE

[75] Inventors: Rémy Teissier, Francheville; Jacques Kervennal, Lyons, both of France

[73] Assignee: Elf Atochem S.A., Puteaux, France

[21] Appl. No.: 808,117

[22] Filed: Feb. 28, 1997

[30] Foreign Application Priority Data

Feb. 29, 1996 [FR] France .................................. 96 02550

[51] Int. Cl.$^6$ .................................................. C07C 45/45
[52] U.S. Cl. ........................................... 568/388; 568/390
[58] Field of Search ...................... 568/388, 390

[56] References Cited

U.S. PATENT DOCUMENTS

| | | | |
|---|---|---|---|
| 2,399,976 | 5/1946 | Ballard | 568/388 |
| 4,458,026 | 7/1984 | Reichle | 568/388 |
| 4,476,324 | 10/1984 | Reichle | 568/388 |
| 4,970,191 | 11/1990 | Schutz | 568/388 |
| 5,055,620 | 10/1991 | Schutz | 568/388 |
| 5,153,156 | 10/1992 | Schutz et al. | 568/388 |
| 5,202,496 | 4/1993 | Schutz et al. | 568/388 |
| 5,254,743 | 10/1993 | Holmgren et al. | 568/388 |

FOREIGN PATENT DOCUMENTS

| | | | |
|---|---|---|---|
| A1-640387 | 3/1995 | European Pat. Off. | 568/388 |
| WO 92/00266 | 1/1992 | WIPO | 568/388 |

OTHER PUBLICATIONS

K.V. Ramanamurty, G.S. Salvapati, M. Janardanarao and R. Vaidyeswaran, Proc. 8th Nat. Symp. Catal., Sindri, India, Feb. 12–14, 1987, pp. 649–660.

*Primary Examiner*—James H. Reamer
*Attorney, Agent, or Firm*—Pennie & Edmonds LLP

[57] ABSTRACT

The present invention relates to a process for obtaining isophorone from acetone, characterized in that the operation is carried out (i) in liquid phase in the presence of a magnesium aluminum double oxide of formula $Mg_{1-x}Al_xO_{1+x}$ or (ii) either in gaseous or liquid phase in the presence of a catalyst of general formula (I):

$$[(Mg^{2+})_{1-x}(Al^{3+})_x(OH^-)_2]^{x+}[(OH^-)_x]^{x-}(H_2O)_n \quad (I)$$

with $0.20 \leq x \leq 0.33$ and $n<1$.

34 Claims, No Drawings

PROCESS FOR OBTAINING ISOPHORONE

1. BACKGROUND OF THE INVENTION

1.1 Technical Field

The present invention relates to a new process for obtaining isophorone from acetone.

1.2 Description of Related Art

Isophorone is employed industrially as a solvent and is also an important synthesis intermediate, especially for the manufacture of 3,5-xylenol. The autocondensation of acetone to isophorone can be performed either in liquid phase or in vapor phase. The liquid phase process generally employs dilute solutions of potassium or sodium hydroxide as catalyst (GB 1528129, BE 611719, U.S. Pat. No. 2,399,976, FR 1506158). However, this process has many disadvantages. The catalysts are not very selective. Only a portion of the catalyst is recycled after settling and separation of the isophorone. The other, unrecycled, portion is neutralized with sulfuric acid and consequently produces salts, the removal of which, necessary for the protection of the environment, is costly.

Furthermore, the autocondensation of acetone in the vapor phase is carried out at elevated temperature, generally higher than 200° C. and in the presence of basic catalysts such as magnesium or aluminum oxides (K. V. Ramanamurthy et al., Proc. 8th Nat. Symp. Catal., Sindri, India, 12–14 Feb. 1987, p. 649) and mixed oxides based on magnesium and aluminum (EP 640387; U.S. Pat. No. 4,970,191). The disadvantages of this vapor phase reaction are numerous.

Thus, the preparation of the catalysts is poorly reproducible and their forming, to avoid diffusion phenomena, is not very easy (U.S. Pat. No. 5,153,166). In addition, the lifetime of these catalysts is reduced by coke deposition at the surface, which is accompanied by non-recyclable heavy by-products.

2. DESCRIPTION OF THE INVENTION

A new process for obtaining isophorone from acetone has now been found, which has the advantage of the ability to employ the existing plants operating in liquid phase without, however, exhibiting the above-mentioned disadvantages. This process is characterized in that the operation is carried out (i) in liquid phase in the presence of a magnesium aluminum double oxide of formula $Mg_{1-x}Al_xO_{1+x}$ or (ii) either in gaseous or liquid phase in the presence of a catalyst of general formula (I):

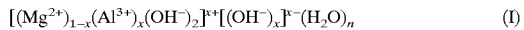
                                                   (I)

with $0.20 \leq x \leq 0.33$ and $n<1$.

The magnesium aluminum double oxide $Mg_{1-x}Al_xO_{1+x}$, which has a value of x that can range from 0.2 to 0.33 may be either a commercial product or one obtained by any conventional methods known to inorganic chemists, such as, for example, by calcining hydrotalcites at a temperature lower than 800° C. Advantageously, a commercial double oxide is employed and preferably that from the Japanese company Kyowa, known as KW 2000, which has an x value close to 0.3.

The catalyst of general formula (I) has a lamellar structure similar to that of hydrotalcite.

Like natural hydrotalcite, this catalyst is composed of positively charged layers of the brucite type, of formula $[Mg_{1-x}Al_x(OH)_2]$ with $0.2 \leq x \leq 0.33$, and of interlayers consisting of hydroxides ($OH^-$) and of water molecules.

The catalyst of general formula (I) which has a value of n that can range from about 0.48 to about 0.75 is preferably employed.

Advantageously, a catalyst of general formula (I) in the case of which the value of n is between about 0.48 and about 0.61, the limits included, is chosen for the reaction of autocondensation of acetone to isophorone, especially meixnerite of formula:

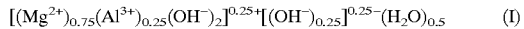
                                                 (I)

The catalyst of general formula (I) can be prepared by following the method described by G. Mascolo and O. Marino in Mineralogical Magazine, March 1980, vol. 43, p. 619.

This method of preparation consists of suspending alumina gel and MgO, obtained by calcining basic magnesium carbonate at 650° C., in distilled water in a closed Teflon receptacle, with stirring, for a week at 80°±1° C. The suspension is then filtered in the absence of $CO_2$ and, lastly, the solid collected is dried over silica gel.

This catalyst can also be prepared by hydration of a magnesium aluminum double oxide in the absence of $CO_2$. The hydration is performed with water either in liquid phase or in vapor phase. The mixed double oxide can be either a commercial product or the product obtained by calcining hydrotalcites which have a value of x that can range from 0.2 to 0.33.

After the hydration stage in accordance with either of the methods described above, the solid can be dried either by evaporation at reduced pressure at a temperature lower than 60° C. or by rinsing with a water-miscible solvent like, for example, acetone.

To prepare the catalyst of general formula (I) a commercial double oxide is advantageously chosen, and preferably the same one as that referred to above.

In most cases the double oxide is hydrated in liquid phase and the solid thus obtained is advantageously rinsed with a water-miscible solvent and preferably with acetone.

Although the catalyst of general formula (I) may be used in the reaction of autocondensation of acetone to isophorone in a vapor phase, it is preferred to employ it in the reaction in a liquid phase.

The process for obtaining isophorone from acetone in accordance with the present invention may be carried out continuously or noncontinuously. Industrially, it is preferred to operate continuously.

When operating continuously, the catalyst may be either placed in a stationary bed through which liquid acetone passes, or brought into contact with liquid acetone in a stirred bed.

Regardless of the manner of operation (continuous or noncontinuous), the pressure must be sufficient to keep the acetone in liquid phase at the temperature of autocondensation. A temperature of between approximately 100° C. and approximately 250° C. is generally employed, and in most cases a temperature of between approximately 110° C. and approximately 220° C. is preferred.

In noncontinuous operation the reaction period may range from 30 minutes to 8 hours and preferably from 1 hour to 4 hours. However, a reaction period longer than 8 hours will not constitute a departure from the scope of the present invention.

At the end of the reaction the isophorone is separated from the by-products by conventional techniques (distillation, settling). The by-products including essentially mesityl oxide, diacetone alcohol and $C_{12}$ and $C_{15}$ compounds can be recycled, and therefore reclaimed.

3. DESCRIPTION OF THE PREFERRED EMBODIMENTS

The invention will be understood better from the following examples:

3.1 Preparation of Catalyst

The mixed double oxide KW 2000 which has the following characteristics is hydrated with water in liquid phase:

Chemical formula: 4.5MgO.Al$_2$O$_3$ (x=0.3077)
Apparent density: 44 ml/10 g
Appearance: odorless fine white powder
BET Surface Area=172 m$^2$/g
Mean particle size: 70 μm
Absorption property: absorbs at most 70–80 parts of water per 100 parts of KW 2000

6 grams of KW 2000 are thus added with stirring to 200 ml of decarbonated water (ion-exchanged, and then boiled, water). The mixture is left stirred for 3 hours and the solid is then separated off. The isolated solid is next rinsed several times with acetone before being stored in the absence of CO$_2$. 9 g of solid are obtained, of general formula (I) where x has the value 0.3077, and which has a crystal structure of the hydrotalcite or of the meixnerite type.

3.2 Catalyst Test

General procedure.

Approximately 50 g to 200 g of acetone and a quantity of solid catalyst of between approximately 1 g and 10 g are introduced at ambient temperature into a stirred and thermostated 0.5-liter autoclave. Next, the autoclave is closed and then purged with nitrogen and, optionally, a nitrogen pressure of up to approximately 20 bars may be applied. Stirring is started to reach a speed of approximately 500 to 1500 revolutions per minute. The mixture is next heated to a temperature of between 110° C. and 220° C. over a period ranging from 30 minutes to 2 hours. The temperature is then maintained for a period of between 1 hour and 4 hours. At the end of the reaction the autoclave is quickly cooled for approximately 5 to 10 minutes with the aid of water circulation. After cooling, the autoclave is opened and the catalyst is separated from the final solution merely by filtration or settling. The final solution containing acetone, diacetone alcohol, mesityl oxide, isophorone and C$_{12}$ and C$_{15}$ compounds is next analyzed with the aid of gas phase chromatography, whereby the final amounts of acetone and isophorone present are determined.

3.3 Chromatography Conditions

A Hewlett-Packard 5710 chromatograph is fitted with an HP1 column of 30 m length and 0.53 mm diameter. The injector temperature is 150° C. and the FID detector temperature is 200° C. The oven is programmed so as to maintain its temperature at 60° C. for 6 minutes and then to increase its temperature at a heating rate of 8° C. per minute until 250° C. is reached.

The acetone conversion is defined by the following formula:

$$\frac{100 \times [(\text{number of moles of acetone})_o - (\text{number of moles of acetone})_f]}{(\text{number of moles of acetone})_o}$$

wherein (number of moles of acetone)$_o$=number of moles of acetone introduced into the reactor; and (number of moles of acetone)$_f$=number of moles of acetone remaining at the end of the reaction.

The selectivity for isophorone is defined by the following formula:

$$\frac{300 \times [(\text{number of moles of } ipho)_f]}{(\text{number of moles of acetone})_o - (\text{number of moles of acetone})_f}$$

wherein (number of moles of ipho)$_f$=number of moles of isophorone formed at the end of the reaction.

3.4 EXAMPLES

Example 1

3 g of KW 2000 catalyst and 100 g of acetone are introduced at ambient temperature into a stirred and thermostated 0.5-liter autoclave. The autoclave is closed and then purged with nitrogen and stirring is started. The mixture is then heated over an hour to a temperature of 150° C. at a stirring rate of 1000 revolutions per minute. The stirred mixture is maintained at 150° C. for one hour and the pressure of the reaction mixture is then at approximately 10 bars. At the end of one hour's reaction at 150° C. the autoclave is cooled over 5 minutes with the aid of water circulation. The cooled autoclave is next opened and the catalyst is separated from the final mixture simply by filtration. The composition of the final solution is determined with the aid of gas phase chromatography.

| The final mixture is composed, in mass %, of | |
|---|---|
| Acetone | 75 |
| Mesityl oxide | 9 |
| Diacetone alcohol | 3 |
| Isophorone | 7.3 |
| C$_{12}$ compounds | 1 |
| C$_{15}$ compounds | 0.8 |
| Unidentified compounds + water | 3.9 |

This corresponds to an acetone conversion of 25% and a selectivity of 37% for isophorone. The total selectivity for C$_{21}$, mesityl oxide, diacetone alcohol and isophorone is 97%.

Example 2

The operation is as in Example 1, except that 6 g of KW 2000 are employed instead of 3 g of KW 2000.

The final composition of the mixture after one hour's reaction is reported in Table 1.

An acetone conversion of 30% and a selectivity for isophorone of 45% are obtained.

Example 3

The procedure is identical with Example 1, except that the autoclave is maintained at 180° C. for one hour and the pressure of the reaction mixture is 18 bars. The final composition of the mixture after one hour's reaction at 180° C. is reported in Table 1.

An acetone conversion of 35.5% and a selectivity for isophorone of 47% are obtained.

Example 4

The procedure is identical with Example 1, except that 102 g of acetone are introduced instead of 100 g and the autoclave is maintained at 200° C. instead of 150° C. The pressure of the reaction mixture is 25 bars.

The final composition is listed in Table 1 and corresponds to an acetone conversion of 37% and a selectivity for isophorone of 48%.

Example 5

The procedure is identical with Example 3, except that a catalyst which has already operated in the same experimental conditions is employed. The composition of the final solution is reported in Table 1.

An acetone conversion of 32% and a selectivity for isophorone of 45% are obtained.

Example 6

The procedure is identical with Example 4, except that 3 g of catalyst hydrated and rinsed in accordance with the method described in Section 3.1 are employed instead of the KW 2000 catalyst. 105 g of acetone are also introduced instead of 102 g. The composition of the final solution is reported in Table 1.

An acetone conversion of 38% and a selectivity for isophorone of 51% are obtained.

Example 7

The procedure is identical with Example 6, except that the temperature is maintained at 120° C. for 4 hours instead of 200° C. for 1 hour. 104 g of acetone are also introduced into the reactor instead of 105 g. The composition of the final solution is reported in Table 1.

An acetone conversion of 25% and a selectivity for isophorone of 24% are obtained.

Example 8

The procedure is identical with Example 7, except that the autoclave is maintained at a temperature of 150° C. instead of 120° C. and that 103 g of acetone are introduced instead of 104 g. The composition of the final solution is reported in Table 1.

An acetone conversion of 31% and a selectivity for isophorone of 45% are obtained.

Example 9 (comparative)

The procedure is identical with Example 3, except that 106 g of acetone are introduced instead of 100 g and that 10 g of water are added to the autoclave. The final composition is reported in Table 1.

An acetone conversion of 11% and a selectivity for isophorone of 45% are obtained.

Example 10

The procedure is identical with Example 1, but the catalyst hydrated and rinsed in accordance with the method described in Section 3.1 is introduced instead of KW 2000. After 1 hour's reaction at 150° C. an acetone conversion of 27% and a selectivity for isophorone of 48% are obtained.

In identical experimental conditions the double oxide is less selective than the hydrated catalyst of general formula (I).

TABLE 1

| Examples | Final composition, mass % | | | | | | |
|---|---|---|---|---|---|---|---|
| | Acetone | Mesityl oxide | Diacetone alcohol | Isophorone | Compounds | | Unidentified compounds + water |
| | | | | | $C_{12}$ | $C_{15}$ | |
| 1 | 75 | 9 | 3 | 7.3 | 1 | 0.8 | 3.9 |
| 2 | 70 | 8 | 3.3 | 10.8 | 1.6 | 1.3 | 5 |
| 3 | 64.5 | 8.2 | 3.2 | 13.2 | 1.7 | 3 | 6.2 |
| 4 | 63 | 8 | 4 | 14 | 1.5 | 3 | 6.5 |
| 5 | 68 | 8 | 3.7 | 11.5 | 1.7 | 1.6 | 5.5 |
| 6 | 61 | 8 | 3 | 14.8 | 2.4 | 3.7 | 7.1 |
| 7 | 75 | 12.7 | 4 | 4.5 | 0.4 | 0.2 | 3.2 |
| 8 | 69 | 8.2 | 3 | 12 | 1.1 | 1.3 | 5.4 |
| 9 | 89 | 4.3 | 2.8 | 1.2 | 0.5 | 0.5 | 1.7 |

We claim:

1. A process for obtaining isophorone from acetone, characterized in that the operation is carried out (i) in liquid phase in the presence of a magnesium aluminum double oxide of formula $Mg_{1-x}Al_xO_{1+x}$ or (ii) either in gaseous or liquid phase in the presence of a catalyst of general formula (I):

$$[(Mg^{2+})_{1-x}(Al^{3+})_x(OH^-)_2]^{x+}[(OH^-)_x]^{x-}(H_2O)_n \qquad (I)$$

with $0.20 \leq x \leq 0.33$ and $n < 1$.

2. The process according to claim 1, characterized in that the value of n is between about 0.48 and about 0.75, the limits included.

3. The process according to claim 1, characterized in that the value of n is between about 0.48 and about 0.61, the limits included.

4. The process according to claim 1, characterized in that the liquid acetone and the catalyst are in contact at a temperature of between about 100° C. and 250° C.

5. The process according to claim 4, characterized in that the temperature is between about 110° C. and about 220° C.

6. A liquid phase process for obtaining isophorone from acetone which comprises:

contacting the liquid acetone with a solid catalyst comprising a magnesium aluminum double oxide of formula $$Mg_{1-x}Al_xO_{1+x};$$

and recovering a product consisting essentially of isophorone, unreacted acetone and by-products;

wherein $0.20 \leq x \leq 0.33$.

7. The process according to claim 6, wherein x is about 0.3.

8. The process according to claim 6, wherein the process is carried out continuously.

9. The process according to claim 8, wherein the liquid acetone passes through a stationary bed comprising the catalyst.

10. The process according to claim 8, wherein the liquid acetone contacts a stirred bed comprising the catalyst.

11. The process according to claim 6, wherein the process is carried out noncontinuously.

12. The process according to claim 11, wherein the liquid acetone and the catalyst are in contact for a reaction period of from 30 minutes to 8 hours.

13. The process according to claim 12, wherein the reaction period is from 1 hour to 4 hours.

14. The process according to claim 6, characterized in that the liquid acetone and the catalyst are in contact at a temperature of between about 100° C. and 250° C.

15. The process according to claim 14, characterized in that the temperature is between about 110° C. and about 220° C.

16. The process according to claim 6, wherein the process further comprises separating the solid catalyst from the product.

17. The process according to claim 16, wherein the method of separating is filtration.

18. The process according to claim 6, wherein the process further comprises separating isophorone from the unreacted acetone and the by-products.

19. The process according to claim 18, wherein the method of separating is selected from distillation and settling.

20. A process for obtaining isophorone from acetone which comprises:

contacting the acetone with a solid catalyst comprising a compound of general formula (I):

$$[(Mg^{2+})_{1-x}(Al^{3+})_x(OH^-)_2]^{x+}[(OH^-)_x]^{x-}(H_2O)_n \qquad (I);$$

and recovering a product consisting essentially of isophorone, unreacted acetone and by-products;

wherein $0.20 \leq x \leq 0.33$ and $n < 1$.

21. The process according to claim 20, characterized in that the acetone is present in a gaseous phase.

22. The process according to claim 20, characterized in that the acetone is present in a liquid phase.

23. The process according to claim 22, wherein the process is carried out continuously.

24. The process according to claim 23, wherein the liquid acetone passes through a stationary bed comprising the catalyst.

25. The process according to claim 23, wherein the liquid acetone contacts a stirred bed comprising the catalyst.

26. The process according to claim 22, wherein the process is carried out noncontinuously.

27. The process according to claim 26, wherein the liquid acetone and the catalyst are in contact for a reaction period of from 30 minutes to 8 hours.

28. The process according to claim 27, wherein the reaction period is from 1 hour to 4 hours.

29. The process according to claim 20, wherein the catalyst comprises a meixnerite compound of formula:

$$[(Mg^{2+})_{0.75}(Al^{3+})_{0.25}(OH^-)_2]^{0.25+}[(OH^-)_{0.25}]^{0.25-}(H_2O)_{0.5}.$$

30. The process according to claim 20, wherein the process further comprises preparing the solid catalyst by a process selected from the group consisting of:

mixing a magnesium aluminum double oxide with water in the absence of $CO_2$ to form a mixture, stirring the mixture, forming a hydrated solid, separating the solid from the mixture, and drying the solid, wherein the magnesium aluminum double oxide has the formula $Mg_{1-x}Al_xO_{1+x}$ wherein $0.20 \leq x \leq 0.33$;

and calcining a hydrotalcite to form a magnesium aluminum double oxide, mixing the magnesium aluminum double oxide with water in the absence of $CO_2$ to form a mixture, stirring the mixture, forming a hydrated solid, separating the solid from the mixture, and drying the solid, wherein the magnesium aluminum double oxide has the formula $Mg_{1-x}Al_xO_{1+x}$ wherein $0.20 \leq x \leq 0.33$.

31. The process according to claim 20, wherein the process further comprises separating the solid catalyst from the product.

32. The process according to claim 31, wherein the method of separating is filtration.

33. The process according to claim 20, wherein the process further comprises separating isophorone from the unreacted acetone and the by-products.

34. The process according to claim 33, wherein the method of separating is selected from distillation and settling.

* * * * *

UNITED STATES PATENT AND TRADEMARK OFFICE
CERTIFICATE OF CORRECTION

PATENT NO. : 5,849,957
DATED : December 15, 1998
INVENTOR(S) : Teissier et al

It is certified that error appears in the above-identified patent and that said Letters Patent is hereby corrected as shown below:

In column 2, line 4, "$[(Mg^{2+})_{0.75}(Al^{3+})_{0.25}(OH^-)_2]^{0.25+}[(OH^-)_{0.25}]^{0.25-}(H_2O)_{0.5}$ (I)" should be changed to --$[(Mg^{2+})_{0.75}(Al^{3+})_{0.25}(OH^-)_2]^{0.25+}[(OH^-)_{0.25}]^{0.25-}(H_2O)_{0.5}$--.

In column 4, line 20, "Unidentified compounds +" should be changed to --Unidentified compounds--.

In column 4, line 21, "water" should be changed to --+ water--.

In column 4, line 26, "$C_{21}$" should be changed to --$C_{12}$--.

Signed and Sealed this

Fifteenth Day of June, 1999

Attest:

Q. TODD DICKINSON

Attesting Officer

Acting Commissioner of Patents and Trademarks